US011291648B2

(12) United States Patent
Elmaleh et al.

(10) Patent No.: US 11,291,648 B2
(45) Date of Patent: Apr. 5, 2022

(54) POWDERED FORMULATIONS OF CROMOLYN SODIUM AND ALPHA-LACTOSE

(71) Applicants: The General Hospital Corporation, Boston, MA (US); AZTherapies, Inc., Boston, MA (US)

(72) Inventors: David R. Elmaleh, Newton, MA (US); Juan B. Gonzalez, Rochester, NH (US)

(73) Assignees: The General Hospital Corporation, Boston, MA (US); AZTherapies, Inc., Boston, MA (US)

(*) Notice: Subject to any disclaimer, the term of this patent is extended or adjusted under 35 U.S.C. 154(b) by 0 days.

(21) Appl. No.: 16/585,871

(22) Filed: Sep. 27, 2019

(65) Prior Publication Data

US 2020/0022947 A1    Jan. 23, 2020

Related U.S. Application Data

(63) Continuation of application No. PCT/US2019/040247, filed on Jul. 2, 2019.

(60) Provisional application No. 62/692,962, filed on Jul. 2, 2018.

(51) Int. Cl.
| | | |
|---|---|---|
| *A61K 31/352* | (2006.01) | |
| *A61K 9/00* | (2006.01) | |
| *A61K 47/12* | (2006.01) | |
| *A61K 47/26* | (2006.01) | |
| *A61K 9/50* | (2006.01) | |

(52) U.S. Cl.
CPC .......... *A61K 31/352* (2013.01); *A61K 9/0075* (2013.01); *A61K 9/50* (2013.01); *A61K 47/12* (2013.01); *A61K 47/26* (2013.01)

(58) Field of Classification Search
None
See application file for complete search history.

(56) References Cited

U.S. PATENT DOCUMENTS

| | | |
|---|---|---|
| 3,419,578 A | 12/1968 | Fitzmaurice et al. |
| 3,634,582 A | 1/1972 | Hartley et al. |
| 3,686,412 A | 8/1972 | Fitzmaurice et al. |
| 3,957,965 A | 5/1976 | Hartley et al. |
| 4,405,598 A * | 9/1983 | Brown ............ A61K 9/008 424/45 |
| 4,405,735 A | 9/1983 | Wiezer et al. |
| 4,429,545 A | 2/1984 | Steinberg |
| 4,481,206 A | 11/1984 | Spiegel et al. |
| 4,996,296 A | 2/1991 | Pecht et al. |
| 5,376,386 A | 12/1994 | Ganderton et al. |
| 5,567,720 A | 10/1996 | Averback |
| 5,594,142 A | 1/1997 | Gaa et al. |
| 5,655,523 A | 8/1997 | Hodson et al. |
| 5,830,920 A | 11/1998 | Chucholowski et al. |
| 5,904,937 A | 5/1999 | Augello et al. |
| 6,168,776 B1 | 1/2001 | Klunk et al. |
| 6,197,963 B1 | 3/2001 | Hirschmann et al. |
| 6,309,623 B1 | 10/2001 | Weers et al. |
| 6,696,039 B2 | 2/2004 | Kung et al. |
| 6,911,466 B2 | 6/2005 | Koo et al. |
| 6,946,116 B2 | 9/2005 | Kung et al. |
| 6,972,127 B2 | 12/2005 | Schenk |
| 7,160,559 B1 | 1/2007 | McGee et al. |
| 7,858,803 B2 | 12/2010 | Elmaleh et al. |
| 8,381,454 B1 | 2/2013 | Robinson |
| 8,613,920 B2 | 12/2013 | Lieberburg et al. |
| 8,617,517 B2 | 12/2013 | Elmaleh et al. |
| 8,765,742 B2 | 7/2014 | Hilfiker et al. |
| 9,283,230 B2 | 3/2016 | Clunas et al. |
| 9,855,276 B2 | 1/2018 | Elmaleh |
| 9,861,608 B2 | 1/2018 | Elmaleh et al. |
| 9,913,847 B2 | 3/2018 | Elmaleh |
| 9,918,992 B2 | 3/2018 | Elmaleh |
| 9,925,282 B2 | 3/2018 | Elmaleh et al. |
| 9,968,618 B1 | 5/2018 | Elmaleh |
| 10,058,530 B2 | 8/2018 | Elmaleh |
| 10,092,564 B2 | 10/2018 | Moussy et al. |
| 10,188,757 B2 | 1/2019 | Elmaleh |
| 10,238,628 B2 | 3/2019 | Gerhart et al. |
| 10,245,331 B2 | 4/2019 | Elmaleh |
| 10,251,961 B2 | 4/2019 | Elmaleh |
| 10,398,704 B2 | 9/2019 | Elmaleh |
| 10,406,164 B2 | 9/2019 | Elmaleh |
| 10,413,551 B2 | 9/2019 | Elmaleh |
| 10,525,005 B2 | 1/2020 | Elmaleh |
| 10,561,612 B2 | 2/2020 | Elmaleh |
| 10,576,171 B2 | 3/2020 | Elmaleh |
| 11,013,686 B2 | 5/2021 | Elmaleh |
| 11,110,097 B2 | 9/2021 | Elmaleh |

(Continued)

FOREIGN PATENT DOCUMENTS

| | | |
|---|---|---|
| CA | 2408793 A1 | 12/2001 |
| CN | 101754746 A | 6/2010 |
| CN | 101848733 A | 9/2010 |
| EP | 1632242 A2 | 3/2006 |
| EP | 2322163 A1 | 5/2011 |

(Continued)

OTHER PUBLICATIONS

Das et al., "Importance of particle size and shape on the tensile strength distribution and de-agglomeration of cohesive powders," Powder Technology 249 (2013) 297-303 (Year: 2013).*

(Continued)

*Primary Examiner* — Aradhana Sasan
(74) *Attorney, Agent, or Firm* — Foley Hoag LLP

(57) ABSTRACT

The present disclosure is directed to a composition comprising micronized cromolyn sodium, α-lactose, and a salt of fatty acid, wherein the α-lactose has a particle size distribution of $D_{90}$ of 45-70 μm, $D_{50}$ of 10-35 μm, and $D_{10}$ of 2-13 μm. The present disclosure is also directed to a method of treating Alzheimer's disease, amyloidosis-associated condition (AAC), traumatic brain injury, Huntington's disease, atherosclerosis, cytokine release syndrome (CRS), dementia, head injury, infection, neuroinflammation, prion disease, stroke, amyotrophic lateral sclerosis (ALS), Parkinson's disease, or asthma using the composition.

27 Claims, No Drawings

(56) References Cited

U.S. PATENT DOCUMENTS

| | | |
|---|---|---|
| 2002/0009491 A1 | 1/2002 | Rothbard et al. |
| 2002/0016359 A1 | 2/2002 | Hellberg et al. |
| 2002/0091100 A1 | 7/2002 | Lezdey et al. |
| 2002/0107173 A1 | 8/2002 | Friedhoff et al. |
| 2004/0176469 A1 | 9/2004 | Thomas |
| 2004/0223918 A1 | 11/2004 | Pham et al. |
| 2004/0259952 A1 | 12/2004 | Abbas et al. |
| 2006/0051319 A1 | 3/2006 | Yoo |
| 2006/0142241 A1 | 6/2006 | Yoo |
| 2006/0159629 A1 | 7/2006 | Tarara et al. |
| 2006/0240007 A1 | 10/2006 | Sanders |
| 2006/0276455 A1 | 12/2006 | Lindsberg et al. |
| 2007/0015813 A1 | 1/2007 | Carter et al. |
| 2007/0086981 A1 | 4/2007 | Meijer et al. |
| 2007/0093457 A1 | 4/2007 | Arber et al. |
| 2007/0178166 A1 | 8/2007 | Bernstein et al. |
| 2007/0193577 A1 | 8/2007 | Keller |
| 2007/0249644 A1 | 10/2007 | Pearson et al. |
| 2007/0293538 A1 | 12/2007 | Hobden |
| 2008/0021085 A1 | 1/2008 | Koo et al. |
| 2009/0110679 A1 | 4/2009 | Li et al. |
| 2009/0155256 A1 | 6/2009 | Black et al. |
| 2010/0113613 A1 | 5/2010 | McLaurin et al. |
| 2010/0143251 A1 | 6/2010 | Tamagnan et al. |
| 2010/0173960 A1 | 7/2010 | Cruz et al. |
| 2010/0234295 A1 | 9/2010 | Chen |
| 2010/0236550 A1 | 9/2010 | Zeng et al. |
| 2010/0266531 A1 | 10/2010 | Hsieh et al. |
| 2010/0298389 A1 | 11/2010 | Elmaleh et al. |
| 2011/0060138 A1 | 3/2011 | Elmaleh et al. |
| 2011/0129530 A1 | 6/2011 | Venkatesh et al. |
| 2011/0262442 A1 | 10/2011 | Hamilton et al. |
| 2012/0058049 A1 | 3/2012 | Elmaleh et al. |
| 2012/0082727 A1 | 4/2012 | Cocconi et al. |
| 2012/0118991 A1 | 5/2012 | Keller et al. |
| 2012/0121656 A1 | 5/2012 | Watson et al. |
| 2012/0134929 A1 | 5/2012 | McGrath et al. |
| 2012/0165366 A1 | 6/2012 | Ibrahim et al. |
| 2012/0308613 A1 | 12/2012 | Staniforth et al. |
| 2013/0197105 A1 | 8/2013 | Pipkin et al. |
| 2014/0140927 A1 | 5/2014 | Elmaleh et al. |
| 2014/0228304 A1 | 8/2014 | Jones et al. |
| 2015/0224077 A1 | 8/2015 | Gerhart et al. |
| 2015/0224078 A1 | 8/2015 | Gerhart et al. |
| 2015/0274680 A1 | 10/2015 | Ueda et al. |
| 2015/0283113 A1 | 10/2015 | Elmaleh |
| 2016/0106704 A1 | 4/2016 | Elmaleh et al. |
| 2016/0158150 A1 | 6/2016 | Morton et al. |
| 2016/0310503 A1 | 10/2016 | Elmaleh |
| 2017/0290797 A1 | 10/2017 | Elmaleh |
| 2018/0169277 A1 | 6/2018 | Elmaleh |
| 2018/0177789 A1 | 6/2018 | Elmaleh |
| 2018/0177790 A1 | 6/2018 | Elmaleh |
| 2018/0177791 A1 | 6/2018 | Elmaleh |
| 2018/0193491 A1 | 7/2018 | Elmaleh |
| 2018/0193492 A1 | 7/2018 | Elmaleh |
| 2018/0344682 A1 | 12/2018 | Elmaleh |
| 2019/0022006 A1 | 1/2019 | Elmaleh et al. |
| 2019/0388568 A1 | 12/2019 | Elmaleh |
| 2020/0022947 A1 | 1/2020 | Elmaleh et al. |
| 2020/0078366 A1 | 3/2020 | Elmaleh |
| 2020/0338040 A1 | 10/2020 | Elmaleh |
| 2020/0383908 A1 | 12/2020 | Elmaleh |
| 2021/0023010 A1 | 1/2021 | Elmaleh et al. |
| 2021/0059977 A1 | 3/2021 | Elmaleh |
| 2021/0085601 A1 | 3/2021 | Elmaleh |

FOREIGN PATENT DOCUMENTS

| | | |
|---|---|---|
| EP | 2377860 A1 | 10/2011 |
| EP | 2911664 B1 | 5/2019 |
| GB | 1144906 A | 3/1969 |
| GB | 1257162 A | 12/1971 |
| JP | 2001-151673 A | 6/2001 |
| JP | 2005-510535 A | 4/2005 |
| JP | 2005/232171 A | 9/2005 |
| JP | 2005532091 A | 10/2005 |
| JP | 2007-534693 A | 11/2007 |
| JP | 2009-536918 A | 10/2009 |
| JP | 2012-515712 A | 7/2012 |
| JP | 2012-516356 A | 7/2012 |
| WO | WO-90/09789 A2 | 9/1990 |
| WO | WO-1997026934 A2 | 7/1997 |
| WO | WO-98/34596 A2 | 8/1998 |
| WO | WO-99/16422 A1 | 4/1999 |
| WO | WO-1999016422 A1 | 4/1999 |
| WO | WO-1999064095 A2 | 12/1999 |
| WO | WO-02/28820 A1 | 4/2002 |
| WO | WO-03/045331 A2 | 6/2003 |
| WO | WO-2004/071532 A1 | 8/2004 |
| WO | WO-2005/063732 A1 | 7/2005 |
| WO | WO-2005/104712 A2 | 11/2005 |
| WO | WO-2007/094718 A1 | 8/2007 |
| WO | WO-2007/102059 A1 | 9/2007 |
| WO | WO-2008/013799 A2 | 1/2008 |
| WO | WO-2008/061373 A1 | 5/2008 |
| WO | WO-2008/128981 A1 | 10/2008 |
| WO | WO-2008/131298 A2 | 10/2008 |
| WO | WO-2009/010770 A2 | 1/2009 |
| WO | WO-2009/133128 A1 | 11/2009 |
| WO | WO-2010/084767 A1 | 7/2010 |
| WO | WO-2010/088455 A2 | 8/2010 |
| WO | WO-2011/136754 A1 | 11/2011 |
| WO | WO-2014/066318 A1 | 5/2014 |
| WO | WO-2015/002703 A1 | 1/2015 |
| WO | WO-2015/061397 A1 | 4/2015 |
| WO | WO-2016/196401 A1 | 12/2016 |
| WO | WO-2017027402 A1 | 2/2017 |
| WO | WO-2017/072335 A1 | 5/2017 |
| WO | WO-2017/087962 A1 | 5/2017 |
| WO | WO-2017/091644 A1 | 6/2017 |
| WO | WO-2017/162884 A1 | 9/2017 |
| WO | WO-2018/045217 A1 | 3/2018 |
| WO | WO-2019/199776 A1 | 10/2019 |
| WO | WO-2020/010049 A1 | 1/2020 |
| WO | WO-2020/051322 A1 | 3/2020 |
| WO | WO-2020/123449 A1 | 6/2020 |
| WO | WO-2021/207060 A1 | 10/2021 |

OTHER PUBLICATIONS

Kumon et al., "Application and Mechanism of Inhalation Profile Improvement of DPI Formulations by Mechanofusion with Magnesium Stearate," Chem. Pharm. Bull. 56(5) 617-625 (2008) (Year: 2008).*

Extended European Search Report for EP Application No. EP 19172666 dated Jan. 10, 2020.

International Search Report and Written Opinion for International Application No. PCT/US19/49733 dated Jan. 13, 2020.

Aisen et al., "Effects of rofecoxib or naproxen vs placebo on Alzheimer disease progression: a randomized controlled trial," JAMA, 289(21):2819-2826 (2003).

Akiyama et al., "Inflammation and Alzheimer's Disease," Neurobiol Aging, 21(3): 383-421 (2000).

Alafuzoff et al., "Lower counts of astroglia and activated microglia in patients with Alzheimer's disease with regular use of non-steroidal anti-inflammatory drugs," J Alzheimers Dis, 2(1):37-46 (2000).

Albert et al., "Effects of age on the clinical pharmacokinetics of ibuprofen," Am J Med, 77(1, Part 1):47-50 (1984).

Albert et al., "Pharmacokinetics of ibuprofen," Am J Med, 77(1A):40-46 (1984).

Aswania et al., "Relative bioavailability of sodium cromoglycate to the lung following inhalation, using urinary excretion," J Clin Pharmacol, 47:613-618 (1999).

Bannwarth et al., "Stereoselective disposition of ibuprofen enantiomers in human cerebrospinal fluid," Br J Clin Pharmacol, 40(3):266-269 (1995).

Basek et al., "Efficacy of an Isotonic Small Droplet Size Nebulized DSCG on Asthma Control in Children," Acta Paediatrica, 99(Suppl 462):115 (2010).

(56) References Cited

OTHER PUBLICATIONS

Beach et al., "Cromolyn sodium toxicity studies in primates," Toxicol Appl Pharmacol, 57(3):367-400 (1981).
Berge et al., "Pharmaceutical salts," J Pharm Sci, 66(1):1-19 (1977).
Bodor et al., "Improved delivery through biological membranes VII. Dermal delivery of cromoglycic acid (cromolyn) via its prodrugs," International Journal of Pharmaceutics, 7(1):63-75(1980).
Bot et al., "Perivascular mast cells promote atherogenesis and induce plaque destabilization in apolipoprotein E-deficient mice," Circulation, 115(19):2516-2525 (2007).
Breitner et al., "Extended results of the Alzheimer's disease anti-inflammatory prevention trial," Alzheimers Dement, 7(4):402-411 (2011).
Breitner, "Alzheimer disease: The changing view," Annals Neurol, 49(3):418-419 (2001).
Broe et al., "Anti-inflammatory drugs protect against Alzheimer disease at low doses," Arch Neurol, 57:1586-1591 (2000).
Bulic et al., "Tau protein and tau aggregation inhibitors," Neuropharmacology, 59: 276-289 (2010).
Byron et al., "Selection and Validation of Cascade Impactor Test Methods," Respiratory Drug Delivery IX, 1:169-178 (2004).
Cacabelos, "Donepezil in Alzheimer's disease: From conventional trials to pharmacogenetics," Neuropsychiatric Disease and Treatment 3(3):303-333 (2007).
Cairns et al., "Synthesis and Structure-Activity Relationships of Disodium Cromoglycate and Some Related Compounds," Journal of Medicinal Chemistry, 15(6):583-589 (1972).
Chen et al., "Current experimental therapy for Alzheimer's Disease," Curr Neuropharmacol, 5(2): 127-134 (2007).
Cole et al., "Mechanisms of action of non-steroidal anti-inflammatory drugs for the prevention of Alzheimer's disease," CNS Neurol Disord Drug Targets, 9(2):140-148 (2010).
Cummings, "Alzheimer's Disease," N Engl J Med, 351(1):56-67 (2004).
Davies, "Clinical pharmacokinetics of ibuprofen. The first 30 years," Clin Pharmacokinet, 34(2):101-154 (1998).
Deiana et al., "Methylthioninium Chloride Versus Rivastigmine and Their Co-Administration Efficacy in Reversing Scopolamine-Induced Cognitive Deficits in a Pharmacological Mouse Model of Alzheimer's Disease," Alzheimer's and Dementia, 4(4, Supplement): T499 (2009).
Doody et al., "Donepezil treatment of patients with MCI: a 48-week randomized, placebo-controlled trial," Neurology, 72(18):1555-1581 (2009).
Dunbar et al., "Dispersion and Characterization of Pharmaceutical Dry Powder Aerosols," Kona, 16:7-45(1998).
Etminan et al., "Effect of non-steroidal anti-inflammatory drugs on risk of Alzheimer's disease: systematic review and meta-analysis of observational studies," Brit Med J, 327:128-131 (2003).
European Search Report for EP Application No. 13848340 dated Feb. 11, 2016.
European Search Report for European Application No. 14819448.3 dated Feb. 2, 2017.
Extended European Search Report for EP Application No. 10736439.0 dated Jun. 12, 2012.
Extended European Search Report for EP Application No. 16867341.6 dated Jun. 13, 2019.
Extended European Search Report for EP Application No. EP 16869210 dated Sep. 19, 2019.
Extended European Search Report for EP Application No. EP 19166810 dated Sep. 23, 2019.
Extended European Search Report, EP 14855211.0, dated May 29, 2017.
Findeis et al., "Design and testing of inhibitors of fibril formation," Methods Enzymol, 309:476-488 (1999).
Findeis et al., "Modified-peptide inhibitors of amyloid β-peptide polymerization," Biochemistry, 38(21):6791-6800 (1999).
Galimberti et al., "Disease-modifying treatments for Alzheimer's disease," Ther Adv Neurol Disord, 4(4): 203-216 (2011).

Garmise, "Novel Dry Powder Preparations of Whole Inactivated Influenza Virus for Nasal Vaccination," Dissertation, University of North Carolina at Chapel Hill (2007).
Gasparini et al., "Non-steroidal anti-inflammatory drugs (NSAIDs) in Alzheimer's disease: old and new mechanisms of action," J Neurochem, 91(3):521-536 (2004).
Gilani et al., "Influence of Formulation Variables and Inhalation Device on the Deposition Profiles of Cromolyn Sodium Dry Powder Aerosols," Daru 12(3):123-130 (2004).
Griffin, "What causes Alzheimer's?" The Scientist, 25:36-40 (2011).
Guchardi et al., "Influence of fine lactose and magnesium stearate on low dose dry powder inhaler formulations," International Journal of Pharmaceutics 348:10-17 (2008).
Guo et al., "Comparison of Delivery Characteristics from a Combination Metered-Dose Inhaler Using the Andersen Cascade Impactor and the Next Generation Pharmaceutical Impactor," J Pharm Sci, 97(8): 3321-3334 (2008).
Gwin et al., "Cromolyn sodium in the treatment of asthma associated with aspirin hypersensitivity and nasal polyps," Chest, 72(2):148-153 (1977).
Haass et al., "Soluble protein oligomers in neurodegeneration: lessons from the Alzheimer's amyloid [beta]-peptide," Nat Rev Mol Cell Biol, 8(2):101-112 (2007).
Hashimoto et al., "Apolipoprotein E, especially apolipoprotein E4, increases the oligomerization of amyloid β peptide," J Neurosci, 32(43):15181-15192 (2012).
Heneka et al., "Acute treatment with the PPARγ agonist pioglitazone and ibuprofen reduces glial inflammation and Aβ1 -42 levels in APPV717I transgenic mice," Brain, 128:1442-1453 (2005).
Hirouchi, "Current status and perspectives on the development of therapeutic agents for Alzheimer's disease," Nihon Yakurigaku Zasshi, 123(6):421-427 (2004).
Hoozemans et al., "Soothing the inflamed brain: effect of non-steroidal anti-inflammatory drugs on Alzheimer's disease pathology," CNS Neurol Disord Drug Targets, 10(1):57-67 (2011).
Hori et al., "A Food and Drug Administration-approved asthma therapeutic agent impacts amyloid β in the brain in a transgenic model of Alzheimer disease," J Biol Chem, 290(4):1966-1978 (2015).
Huang et al., "Acute stress induces cardiac mast cell activation and histamine release, effects that are increased in Apolipoprotein E knockout mice.," Cardiovasc Res, 55(1):150-160 (2002).
Huang et al., "Stress-induced interleukin-6 release in mice is mast cell-dependent and more pronounced in Apolipoprotein E knockout mice," Cardiovasc Res, 59(1):241-249 (2003).
Imbimbo et al., "Are NSAIDs useful to treat Alzheimer's disease or mild cognitive impairment?," Front Aging Neurosci, 2(19):1-14 (2010).
Imbimbo, "An update on the efficacy of non-steroidal anti-inflammatory drugs in Alzheimer's disease," Expert Opinion on Investigational Drugs, 2009; 18(8), pp. 1147-1168.
InnoPharmalabs, "Particle Size Distribution", Apr. 9, 2013 (Apr. 9, 2013).
Intal Approval Package, Center for Drug Evaluation and Research, application 75-175, pp. 1-5 (Dec. 12, 1997).
International Search Report and Written Opinion for International Application No. PCT/US16/63143 dated Feb. 6, 2017.
International Search Report and Written Opinion for International Application No. PCT/US16/63462 dated Feb. 1, 2017.
International Search Report and Written Opinion for International Application No. PCT/US17/65727 dated Feb. 12, 2018.
International Search Report and Written Opinion for International Application No. PCT/US2010/022495 dated Nov. 10, 2010.
International Search Report and Written Opinion for International Application No. PCT/US2014/061694 dated Jan. 2, 2015.
International Search Report and Written Opinion for International Application No. PCT/US2017/049702 dated Dec. 26, 2017.
International Search Report and Written Opinion for International Application No. PCT/US2019/026521 dated Jun. 14, 2019.
International Search Report and Written Opinion for International Application No. PCT/US2019/40247 dated Sep. 20, 2019.
International Search Report for International Application No. PCT/US2013/066069 dated Mar. 13, 2014.

(56) References Cited

OTHER PUBLICATIONS

International Search Report for International Application No. PCT/US14/39118 dated Sep. 18, 2014.
Jin et al., "Mast cells are early responders after hypoxia-ischemia in immature rat brain," Stroke, 40(9):3107-3112 (2009).
Karran et al., "The amyloid cascade hypothesis for Alzheimer's disease: an appraisal for the development of therapeutics," Nat Rev, 10(9):698-712 (2011).
Keller et al., "Have inadequate delivery systems hampered the clinical success of inhaled disodium cromoglycate? Time for reconsideration," Exp Opin Drug Deliv, 8(1):1-17 (2011).
Kelley et al., "The molecular role of mast cells in atherosclerotic cardiovascular disease," Mol Med Today, 6:304-308 (2000).
Knowles, "Donepezil in Alzheimer's disease: an evidence-based review of its impact on clinical and economic outcomes," Core Evid, 1(3):195-219 (2006).
Kohman et al., "Neurogenesis, inflammation and behavior," Brain Behav Immun, 27C:22-32 (2013).
Koo et al., "Amyloid diseases: Abnormal protein aggregation in neurodegeneration," PNAS, 96:9989-9990(1999).
Kotilinek et al., "Cyclooxygenase-2 inhibition improves amyloid-$\beta$-mediated suppression of memory and synaptic plasticity," Brain, 131(3):651-664 (2008).
Koudstaal et al., "Secondary Stroke Prevention in Atrial Fibrillation: Indications, Risks, and Benefits," J Thromb Thrombolys, 7(1):61-65 (1999).
Krstic et al., "Deciphering the mechanism underlying late-onset Alzheimer disease," Nat Rev Neurol, 9:25-34(2013).
Kwong et al., "Comparison of Nebulized Particle Size Distribution with Malvern Laser Diffraction Analyzer Versus Andersen Cascade Impactor and Low-Flow Marple Personal Cascade Impactor," J Aerosol Med, 13(4): 303-314 (2000).
Lanz et al., "The y-Secretase Inhibitor N-[N-(3,5-Difluorophenacetyl)-L-alanyl]-S-phenylglycine t-butyl Ester Reduces A$\beta$ Levels in Vivo in Plasma and Cerebrospinal Fluid in Young (Plaque-Free) and Aged (Plaque-Bearing) Tg2576 Mice," The Journal of Pharmacology and Experimental Therapeutics, 305(3):864-871 (2003).
Libby, "Inflammation in atherosclerosis," Nature, 420(6917):868-874 (2002).
Lim et al., "Ibuprofen Suppresses Plaque Pathology and Inflammation in a Mouse Model of Alzheimer's Disease," The Journal of Neuroscience 20(15):5709-5714 (2000).
Loeb et al., "A randomized, controlled trial of doxycycline and rifampin for patients with Alzheimer's disease," J Am Geriatr Soc, 52(3): 381-7 (2004).
Mackenzie et al., "Nonsteroidal anti-inflammatory drug use and Alzheimer-type pathology in aging," Neurology, 50(4):986-990 (1998).
Mandel, "CERE-110, an adeno-associated virus-based gene delivery vector expressing human nerve growth factor for the treatment of Alzheimer's disease," Curr Opin Mol Ther, 12(2): 240-247 (2010).
Marinkovic et al., "Evolution of Intracerebral Hemorrhage after Intravenous Tpa: Reversal of Harmful Effects with Mast Cell Stabilization," J Cerebr Blood F Met, 34(1):176-181 (2014).
Mash et al., "Loss of M2 muscarine receptors in the cerebral cortex in Alzheimer's disease and experimental cholinergic denervation," Science, 228(4703):1115-1117 (1985).
McKittrick et al., "Mast Cells Promote Blood Brain Barrier Breakdown and Neutrophil Infiltration in a Mouse Model of Focal Cerebral Ischemia," J Cerebr Blood F Met, 35(4):638-647 (2015).
McLaurin et al., "Cyclohexanehexol inhibitors of A$\beta$ aggregation prevent and reverse Alzheimer phenotype in a mouse model," Nat Med, 12(7):801-808 (2006).
Mitchell et al., "Aerodynamic Particle Size Analysis of Aerosols from Pressurized Metered-Dose Inhalers: Comparison of Andersen 8-Stage Cascade Impactor, Next Generation Pharmaceutical Impactor, and Model 3321 Aerodynamic Particle Sizer Aerosol Spectrometer," AAPS PharmSciTech, 4(4): Article 54 (2003).
Mor et al., "Mast cells and atherosclerosis," Israel Med Assoc J, 3:216-221 (2001).
Morihara et al., "Ibuprofen Suppresses Interleukin-1$\beta$ Induction of Pro-Amyloidogenic $\alpha_1$-Antichymotrypsin to Ameliorate $\beta$-Amyloid (A$\beta$) Pathology in Alzheimer's Models," Neuropsychopharmacology 30:1111-1120 (2005).
Moss et al., "The absorption and clearance of disodium cromoglycate from the lung in rat, rabbit, and monkey," Toxicol Appl Pharmacol, 17(3):699-707 (1970).
Murphy, "Cromolyn sodium: basic mechanisms and clinical usage," Pediatric Asthma, Allergy, and Immunology, 2(4):237-254 (1988).
Neale et al., "The pharmacokinetics of sodium cromoglycate in man after intravenous and inhalation administration," Br J Clin Pharmacol, 22:373-382 (1986).
Netzer et al., "The actual role of sodium cromoglycate in the treatment of asthma—a critical review," Sleep Breath, 16:1027-1032 (2012).
Newman et al., "Therapeutic Aerosols 1—Physical and Practical Considerations," Thorax, 38(12): 881-886 (1983).
Notice of Allowance and Fees Due for U.S. Appl. No. 15/830,980, "Methods for Delivering Cromolyn," dated Aug. 6, 2019.
Notice of Allowance and Fees Due for U.S. Appl. No. 15/838,753, "Powdered Formulations of Cromolyn Sodium and Ibuprofen," dated Oct. 2, 2019.
Obici et al., "AA amyloidosis: basic knowledge, unmet needs and future treatments," Swiss Medical Weekly, 142:w13580 (2012).
Ono et al., "Push-pull benzothiazole derivatives as probes for detecting $\beta$-amyloid plaques in Alzheimer's brains," Bioorg Med Chem, 17(18):7002-7007 (2009).
Palacios et al., "The pharmacological assessment of RS 86 (2-ethyl-8-methyl-2,8-diazaspiro-[4,5]-decan-1,3-dion hydrobromide). A potent, specific muscarinic acetylcholine receptor agonist," Eur J Pharmacol, 125(1):45-62 (1986).
Panza et al., "Immunotherapy for Alzheimer's Disease: From anti-$\beta$-amyloid to tau-based Immunization strategies," Immunotherapy, 4(2):213-238 (2012).
Parepally et al., "Brain uptake of nonsteroidal anti-inflammatory drugs: ibuprofen, flurbiprofen, and indomethacin," Pharm Res, 23(5):873-881 (2006).
Petersen et al., "Vitamin E and donepezil for the treatment of mild cognitive impairment," N Engl J Med, 352(23):2379-2388 (2005).
Pratico, "Alzheimer's disease and non-steroidal anti-inflammatory drugs: Old therapeutic tools with novel mechanisms of action?" Current Medicinal Chemistry—Central Nervous System Agents 5(2):111-117 (2005).
Péhourcq et al., "Diffusion of arylpropionate non-steroidal anti-inflammatory drugs into the cerebrospinal fluid: a quantitative structure-activity relationship approach," Fundamental and Clinical Pharmacology, 18(1):65-70 (2004).
Reagan-Shaw et al., "Dose Translation from Animal to Human Studies Revisited," The FASEB, 22: 659-661 (2007).
Reverchon et al., "Production of Cromolyn Sodium Microparticles for Aerosol Delivery by Supercritical Assisted Atomization," AAPS PharmSciTech 8(4), Article 114 (2007).
Richards et al., "Absorption and disposition kinetics of cromolyn sodium and the influence of inhalation technique," J Pharmacol Exp Ther, 241(3):1028-1032 (1987).
Rousselet et al., "Mouse Model of Intraluminal MCAO: Cerebral Infarct Evaluation by Cresyl Violet Staining," J Vis Exp, 69:e4038 (2012).
Sabbagh et al., "Latrepirdine, a potential novel treatment for Alzheimer's disease and Huntington's chorea," Curr Opin Investig Drugs, 11(1): 80-91 (2010).
Schnabel, J. "Early Results of Alzheimer's Passive Vaccine Trial Mixed," http://www.dana.org/News/Details.aspx?id=42815 printed Jan. 19, 2017, pp. 1-3 (2008).
Schneider et al., "Current Alzheimer's disease clinical trials: methods and placebo outcomes," Alzheimers Dement, 5(5):388-397 (2009).
Shin et al., "Interpretation of Animal Dose and Human Equivalent Dose for Drug Development," Journal of Korean Oriental Medicine, 31(3):1-7 (2010).
STN database CAS RN: 16110-51-3 (Nov. 16, 1984).

(56) References Cited

OTHER PUBLICATIONS

Strejan et al., "Suppression of chronic-relapsing experimental allergic encephalomyelitis in strain-13 guinea pigs by administration of liposome-associated myelin basic protein," J Neuroimmunol, 7(1):27-41 (1984).
Sun et al., "Mast cells promote atherosclerosis by releasing proinflammatory cytokines," Nat Med, 13(6):719-724 (2007).
Sun et al., "Synthesis of scyllo-inositol derivatives and their effects on amyloid beta peptide aggregation," Bioorganic & Medicinal Chemistry 16:7177-7184 (2008).
Taverni et al., "Donepezil medicated memory improvement in traumatic brain injury during post acute rehabilitation," Brain Inj, 12(1):77-80 (1998).
Thal et al., "A randomized, double-blind, study of rofecoxib in patients with mild cognitive impairment," Neuropsychopharmacology, 30:1204-1215 (2005).
Tronde et al., "Pulmonary absorption rate and bioavailability of drugs in vivo in rats: structure-absorption relationships and physicochemical profiling of inhaled drugs," J Pharm Sci, 92(6):1216-1233 (2003).
Upadhyaya, P. et al., "Therapy of Alzheimer's disease: An update," African Journal of Pharmacy and Pharmacology 4(6):408-421 (2010).
Veld et al., "Nonsteroidal antiinflammatory drugs and the risk of Alzheimer's disease," N Engl J Med, 345(21):1515-1521 (2001).
Wang et al. "Allopregnanolone reverses neurogenic and cognitive deficits in mouse model of Alzheimer's disease," PNAS, 107(14): 6498-6503 (2010).
Weggen et al., "A subset of NSAIDs lower amyloidogenic Aβ42 independently of cyclooxygenase activity," Nature, 414(6860):212-216 (2001).
Wettstein et al., "Clinical trials with the cholinergic drug RS 86 in Alzheimer's disease (AD) and senile dementia of the Alzheimer type (SDAT)," Psychopharmacology, 84(4):572-573 (1984).
Wikipedia, "Cromoglicic acid", Aug. 22, 2017 (Aug. 22, 2017), retrieved on Sep. 3, 2019 from https://en.wikipedia.org/w/index.php?title=Cromoglicic_acid&oldid=796733877.
Xiao et al., "Progress of Inhaled Devices for Asthma," Journal of Applied Clinical Pediatrics, 22(4):309-311 (2007).
Yan et al., "Anti-inflammatory drug therapy alters β-amyloid processing and deposition in an animal model of Alzheimer's disease," J Neurosci, 23:7504-7509 (2003).
Zhang et al., "Cromolyn Reduces Levels of the Alzheimer's Disease-Associated Amyloid β-Protein by Promoting Microglial Phagocytosis," Sci Rep, 18; 8(1):1144 (2018).
Zhou et al., "Drug-lactose binding aspects in adhesive mixtures: controlling performance in dry powder inhaler formulations by altering lactose carrier surfaces," Adv Drug Deliv Rev, 64(3):275-284 (2012).
Zlokovic, "Neurovascular pathways to neurodegeneration in Alzheimer's disease and other disorders," Nat Rev Neurosci, 12(12):723-738 (2011).
Certificate of Analysis for Lactohale LH 201, Alpha-Lactose Monohydrate EP and USP, Full Release (DFE Pharma); Jan. 18, 2016.
ClinicalTrials.gov. Phase 1 Study of ALZT-OP1 Combination Therapy in Normal Healthy Volunteers. Sponsor: AZTherapies, Inc. Identifier: NCT02482324. Retrieved Apr. 9, 2020 from: http://clinicaltrials.gov/ct/show/NCT02482324?order=1.
ClinicalTrials.gov. Safety and Efficacy of ALZT-OP1a as Adjuvant Treatment in Subjects With Post-Ischemic Stroke Cognitive Impairment (PSCI). Sponsor: AZTherapies, Inc. Identifier: NCT03202147. Retrieved Feb. 6, 2020, 2020 from: https://clinicaltrials.gov/ct2/show/NCT03202147?term=cromolyn&draw=3&rank=11.
ClinicalTrials.gov. Safety and Efficacy Study of ALZT-OP1 in Subjects With Evidence of Early Alzheimer's Disease (COGNITE). Sponsor: AZTherapies, Inc. Identifier: NCT02547818. Retrieved Apr. 9, 2020 from: https://clinicaltrials.gov/ct2/show/study/NCT02547818?term=AZTherapies&draw=2&rank=1.
ClinicalTrials.gov. Treatment of Acute Stroke With Cromolyn(Single Dose). Sponsor: Wolfson Medical Center. Identifier: NCT01175525. Retrieved Feb. 6, 2020 from: https://clinicaltrials.gov/ct2/show/NCT01175525.
Hensley, "Neuroinflammation in Alzheimer's Disease: Mechanisms, Pathologic Consequences, and Potential for Therapeutic Manipulation," J Alzheimers Dis, 21(1):1-14 (2010).
International Search Report and Written Opinion for International Application No. PCT/US19/65384 dated Mar. 31, 2020.
PubChem CID: 27503, "Cromolyn sodium", Created Jun. 24, 2005. Retreived from the Internet < URL: https://pubchem.ncbi.nlm.nih.gov/compound/Cromolyn-sodium>.
PubChem CID:204318, "Diethyl Cromoglycate," Created Aug. 9, 2005. Retrieved from the Internet <URL: https://pubchem.ncbi.nlm.nih.gov/compound/204318>.
"Stages of ASL" ALS Association Texas Chapter, Retrieved online <https://www.alstexas.org/understanding-als/stages/>: 4 pages (2019).
Cowell, R.M. et al., "Hypoxic-ischemic injury induces macrophage inflammatory protein-1alpha expression in immature rat brain," Stroke (2002) 33,795-801.
Cruz M.P., "Edaravone (Radicava): A novel neuroprotective agent for the treatment of amyotrophic lateral sclerosis," P&T. (2018) 43(1):25-28.
Denes, A. et al., "Proliferating resident microglia after focal cerebral ischaemia in mice," J. Cereb. Blood. Flow. Metab. (2007) 27, 1941-1953.
Desmond, D.W. et al., "Frequency and clinical determinants of dementia after ischemic stroke." Neurology (2000), 54, 1124-1131.
EPAR (European Public Assessment Report) Seebri Breezhaler: Retrieved online at <http://www.ema.europa.eu/ema/index.jsp?curl=pages/medicines/human/medicines/002430/human_med_001580.jsp&mid=WC0b01acQ58001d124>: 6 pages (2012).
Extended European Search Report for EP Application No. EP 17847576 dated Jun. 30, 2020.
Fiala, M. et al., "IL-17A is increased in the serum and in spinal cord CD8 and mast cells of ALS patients," J Neuroinflammation. (2010) 7:76.
Franzius, D., et al., "Non-specific effects of calcium entry antagonists in mast cells," Pflugers Arch. (1994) 428(5-6):433-438.
Ghasemi. M. and Brown. R.H. Jr. "Genetics of amyotrophic lateral sclerosis," Cold Spring Harb. Perspect. Med. (2018) 8(5).
Gorelick, P.B. et al., "Vascular Contributions to Cognitive Impairment and Dementia, A Statement for Healthcare Professionals from the American Heart Association/American Stroke Association," Stroke (2011) 42, 2672-2713.
Granucci. E.J. et al., "Cromolyn sodium delays disease onset and is neuroprotective in the SQD1G93A mouse model of amyotrophic lateral sclerosis." Sci Rep. (2019) 9(1):17728.
Gudesblatt et al., "Hexosaminidase A activity and amyotrophic lateral sclerosis," Muscle and Nerve, II: 227-230 (1988).
Guo, J. et al., "Evaluating the levels of CSF and serum factors in ALS," Brain Behav. (2017) 7:e00637.
Hu et al., "Increased peripheral blood inflammatory cytokine levels in amyotrophic lateral sclerosis: a meta-analysis study," Scientific Reports, 7: Article No. 9094 (2017).
Ihle-Hansen, H. et al., "Incidence and subtypes of MCI and dementia 1 year after first-ever stroke in patients without pre-existing cognitive impairment," Dement. Geriatr. Cogn. Disord. (2011) 32, 401-407.
Ilieva, H., et al., "Non-cell autonomous toxicity in neurodegenerative disorders: ALS and beyond," J. Cell Biol. (2009) 187(6):761-772.
Imbimbo, B.P. et al., "Are NSAIDs useful to treat Alzheimer's disease or mild cognitive impairment?," Front. Aging Neurosci (2010) 2 (article 19), 1-14.
Intal® Nebulizer Solution (Label 2016): Retrieved online at <http://labeling.pfizer.com/ShowLabeling.aspx?id=833>: 4 pages (2016).
International Preliminary Report on Patentability for International Application No. PCT/US2019/040247 dated Jan. 14, 2021.
Jin, R. et al., "Inflammatory mechanisms in ischemic stroke: role of inflammatory cells," J Leukoc Bio (2010) 87, 779-789.
Kaur et al., "Drug Therapy in Stroke: From Preclinical to Clinical Studies," Pharmacology, 92:234-334(2013).

(56) References Cited

OTHER PUBLICATIONS

Kilpatrick et al., "Cromolyn inhibits assembly of the NADPH oxidase and superoxide anion generation by human neutrophils," *The Journal of Immunology*, 154(7): 3429-3436 (1995).
Krueger, M. et al., "Blood-brain barrier breakdown involves four distinct stages of vascular damage in various models of experimental focal cerebral ischemia," *J. Cereb. Blood Flow Metab.* (2015), 35, 292-303.
Kuhle, J. et al., Increased levels of inflammatory chemokines in amyotrophic lateral sclerosis, *Eur J Neurol.* (2009) 16:771-774.
Lalancette-Hébert, M. et al., "Selective ablation of proliferating microglial cells exacerbates ischemic injury in the brain," *J Neurosci* (2007) 27, 2596-2605.
Lasiene, J and Yamanaka, K., "Glial cells in amyotrophic lateral sclerosis," *Neurol Res Int.* (2011)2011: Article ID 718987.
Liu et al., "Elevated Levels of IFN-γ in CSF and Serum of Patients with Amyotrophic Lateral Sclerosis," Plos One, 10(9): 11 pages (2015).
Material Safety Data Sheet Cromolyn Sodium: Retrieved online at<https://www.biobasic.com/amfilerating/file/download/file_id/24861/http://www.alli.wnyric.org/District/Documents/msds/files/cjx/cjxjy.html>: 5 pages (2017).
Nagoshi, N. et al., "Riluzole as a neuroprotective drug for spinal cord injury: from bench to bedside," *Molecules.* (2015) 20(5):7775-7789.
Nakajima, K. and Kohsaka, S., "Microglia: activation and their significance in the central nervous system," *J Biochem* (2001) 130, 169-175.
Nihashi, T. et al., "Expression and distribution of beta amyloid precursor protein and beta amyloid peptide in reactive astrocytes after transient middle cerebral artery occlusion," *Acta Neurochir (Wien).* (2001) 143, 287-295.
Nys, G.M. et al., "Restrictions of the Mini-Mental State Examination in acute stroke." *Arch Clin Neuropsychol* (2005) 20, 623-629.
Package Insert Intal® (Label 2003): Retrieved online at http://www.accessdata.fda.gov/drugsatfda_docs/label/2004/18887slr020_intal_lbl.pdf.
Parrella, E. et al., "The Role of Mast Cells in Stroke," *Cells* 8.5 (2019), 437 (22 pages).
Patkai, J. et al., "Deleterious effects of IL-9-activated mast cells and neuroprotection by antihistamine drugs in the developing mouse brain," *Pediatr. Res.* (2001) 50, 222-230.
Pluta, R. et al., "Brain ischemia activates β- and γ-secretase cleavage of amyloid precursor protein: significance in sporadic Alzheimer's disease," *Mol Neurobiol.* (2013) 47, 425-434.
Renton. A.E. et al., "State of play in amyotrophic lateral sclerosis genetics," *Nat. Neurosci.* (2014) 17:17-23.
Roberts et al., "Next Generation Pharmaceutical Impactor (A New Impactor for Pharmaceutical Inhaler Testing). Part I: Design," Journal of Aerosol Medicine, 16(3): 283-299 (2003).
Romanin. C., et al., "Immunologically activated chloride channels involved in degranulation of rat mucosal mast cells," *EMBO J.* (1991) 10(12):3603-3608.
Rosen et al., "Mutations in Cu/Zn superoxide dismutase gene are associated with familial amyotrophic lateral sclerosis," *Nature*, 362: 59-62 (1993).
Rothwell, N. et al., "The role of interleukin 1 in acute neurodegeneration and stroke: pathophysiological and therapeutic implications," *J Clin Invest* (1997) 100, 2648-2652.
Selkoe, D.J., "Alzheimer's disease: genes, proteins, and therapy," *Physiol Rev.* (2001) 81, 741-766.
Strbian et al., "Cerebral mast cells regulate early ischemic brain swelling and neutrophil accumulation," *J. Cereb. Blood Flow Metab.* 26:605-612 (2006).
Strbian et al., "Mast Cell Stabilization Reduces Hemorrhage Formation and Mortality After Administration of Thrombolytics in Experimental Ischemic Stroke," Circulation, 116(4):411-418 (2007).
Strbian, D. et al., "An emerging role of mast cells in cerebral ischemia and hemorrhage," *Ann Med* (2009) 41, 438-450.
Strbian, D. et al., "Mast cell blocking reduces brain edema and hematoma volume and improves outcome after experimental intracerebral hemorrhage," *J. Cereb. Blood Flow Metab.* (2007) 27, 795-802.
Sun, J.H. et al., "Post-stroke cognitive impairment: epidemiology, mechanisms and management," *Ann Transl Med* (2014) 2(8): 80 (16 pages).
Szabo, K. et al., "Hippocampal lesion patterns in acute posterior cerebral artery stroke: clinical and MRI findings," *Stroke* (2009) 40, 2042-2045.
Trias, E., et al., "Significance of aberrant glial cell phenotypes in pathophysiology of amyotrophic lateral sclerosis," *Neurosci. Lett.* (2017) 636: 27-31.
Vu et al., "Fluid-Based Biomarkers for Amyotrophic Lateral Sclerosis," *Neurotherapeutics*, 14: 119-134 (2017).
Wisniewski et al., "Immunotherapeutic Approaches for Alzheimer's Disease," *Neuron*, 85(6): 1162-1176 (2015).
Yan, S.D. et al., "RAGE-Aβ interactions in the pathophysiology of Alzheimer's disease," *Restor Neurol Neurosci.* (1998) 12, 167-173.
Yilmaz, G. et al., "Role of T lymphocytes and interferon-γ in ischemic stroke," *Circulation* (2006) 113, 2105-2112.
Yokota et al., "Roles of mast cells in the pathogenesis of inflammatory myopathy," *Arthritis Research Therapy*, 16(R72): 13 pages (2014).
Zhang et al., "Mast cell tryptase induces microglia activation via protease-activated receptor 2 signaling," Cellular Physiology and Biochemistry, 29: 931-940 (2012).
Zhang, R. et al., "Evidence for systemic immune system alterations in sporadic amyotrophic lateral sclerosis (sALS)," *J Neuroimmunol.* (2005) 159(1-2): 215-224.
Zhang, S. et al., "Cerebral mast cells contribute to postoperative cognitive dysfunction by promoting blood brain barrier disruption," *Behavioural Brain Research* (2016) 298, 158-166.
Zhang, X. et al., "Activated brain mast cells contribute topostoperative cognitive dysfunction by evoking microglia activation and neuronal apoptosis," *Journal of Neuroinflammation* (2016) 13: 127 (15 pages).
Zhang, X. et al., "Cerebral mast cells participate in postoperative cognitive dysfunction by promoting astrocyte activation," *Cellular Physiology and Biochemistry* (2016) 40, 104-116.
Mohammed et al., "Effect of Sampling volume on Dry Powder Inhaler (DPI)-Emitted Aerosol Aerodynamic Particle Size Distributions (APSDs) Measured by the Next-Generation Pharmaceutical Impactor (NGI) and the Andersen Eight-Stage Cascade Impactor (ACI)," APPS PharmSciTech, 13(3): 875-882 (2012).
Omer et al., "Comparison between the next generation impactor and the twin glass impinge as model pulmonary drug delivery devices," Zanco J. Med. Sci., 23(1): 74-80 (2019).
Abraham et al., "Mast cell-orchestrated immunity to pathogens," Nat Rev Immunol, 10: 440-452 (2010).
Aloisi F. "Immune function of microglia". *Glia* (2001) 36, 165-179.
Banati, R. B. et al., "Cytotoxicity of microglia". *Glia* (1993) 7, 111-118.
Barone, F.C. et al., "Tumor necrosis factor-α: a mediator of focal ischemic brain injury". *Stroke* (1997) 28, 1233-1244.
Beigel JH, et al. "Remdesivir for the treatment of Covid-19—preliminary report," The New England Journal of Medicine: 1-12 (2020).
Bona, E. et al., "Chemokine and inflammatory cell response to hypoxia-ischemia in immature rats". *Pediatr. Res.* (1999) 45, 500-509.
Butovsky et al., "Identification of a unique TGF-β-dependent molecular and functional signature in microglia," Nat Neurosci, 17(3): 131-143 (2014).
Cherry et al., "Neuroinflammation and M2 microglia: the good, the bad, and the inflamed," J Neuroinflammation, 11(98): 1-15 (2014).
Choi et al., "A three-dimensional human neural cell culture model of Alzheimer's disease," Nature, 515:274-278 (2014).
Cox et al., "Disodium Cromoglycate (FPL 670) ('Intal'*): A Specific Inhibitor of Reaginic Antibody—Antigen Mechanisms," Nature, 216: 1328-1329 (1967).

(56) References Cited

OTHER PUBLICATIONS

Dello Russo et al., "The human microglial HMC3 cell line: where do we stand? A systematic literature review," J Neuroinflammation, 15: 259 (24 pages) (2018).
Du et al., "Role of Microglia in Neurological Disorders and Their Potentials as a Therapeutic Target," Mol Neurobiol, 54: 7567-7584 (2017).
Dubbelaar et al., "The Kaleidoscope of Microglial Phenotypes," Front Immunol, 9: 1753 (2018).
Elmaleh, D.R. et al., "Evaluation of F-18 Radiolabeled Cromolyn as a Potential Aβ Polymerization Inhibitor and PET Tracer". Poster at *Human Amyloid Image (HAI) Conference*, Miami, Florida, Jan. 2014.
Extended European Search Report for EP Application No. 17934303 dated Aug. 13, 2021.
Extended European Search Report for EP Application No. EP 17918310 dated Mar. 12, 2021.
Francesch et al., "Chronic inflammation (inflammaging) and its potential contribution to age-associated diseases," J Gerontol A Biol Sci Med Sci, 69(S1): S4-9 (2014).
Gadani et al., "IL-4 in the brain: a cytokine to remember," J Immunol, 189(9): 4213-4219 (2012).
Gilead Announces Approval of Veklury (remdesivir) in Japan for Patients With Severe COVID-19. The press release of Gilead Sciences. May 7, 2020. URL: < https://www.gilead.com/news-and-press/press-room/press-releases/2020/5/gilead-announces-approval-of-veklury-remdesivir-in-japan-for-patients-with-severe-covid19>. Retrieved on Jul. 14, 2021.
Gomperts et al., "Imaging amyloid deposition in Lewy body disease," Neurology, 71(12): 903-910(2008).
Gosselin et al., "An environment-dependent transcriptional network specifies human microglia identity," Science, 356: eaal3222 (2017).
Granucci et al., "Cromolyn sodium delays disease onset and is neuroprotective in the SOD1G93A Mouse Model of amyotrophic lateral sclerosis," Sci Rep, 9: 17728 (17 pages) (2019).
Granucci et al., "Inducible IL-2 production by dendritic cells revealed by global gene expression analysis," Nat Immunol, 2(9): 882-888 (2001).
Greenhalgh et al., "Immune cell regulation of glia during CNS injury and disease," Nat Rev Neurosci, 21: 139-152 (2020).
Grenier et al., "Three-dimensional modeling of human neurodegeneration: brain organoids coming of age," Mol Psychiatry, 25: 254-274 (2020).
Hallenbeck, J.M. "The many faces of tumor necrosis factor in stroke". *Nat Med* (2002) 8, 1363-1368.
Hemonnot et al., "Microglia in Alzheimer Disease: Well-Known Targets and New Opportunities," Front Aging Neurosci, 11:233(20 pages) (2019).
Holian et al., "Mechanistic aspects of cromolyn sodium action on the alveolar macrophage: inhibition of stimulation by soluble agonists," Agents Actions, 33: 318-325 (1991).
Hopperton et al., "Markers of microglia in post-mortem brain samples from patients with Alzheimer's disease: a systematic review," Mol Psychiatry, 23: 177-198 (2018).
Hori et al., "A Food and Drug Administration-approved asthma therapeutic agent impacts amyloid beta in the brain in a transgenic model of Alzheimer disease," J Biol Chem, 290(4): 1966-1978 (2015).
International Search Report and Written Opinion for International Application No. PCT/US2021/025746 dated Jun. 17, 2021.
International Search Report and Written Opinion for International Application No. PCT/US2021/035936 dated Jul. 22, 2021.
Jellinger, K.A., "Alzheimer disease and cerebrovascular pathology: an update". *J. Neural. Transm.* (2002) 109, 813-836.
Jin, Y. et al., "Mast cell stabilization limits hypoxic-ischemic brain damage in the immature rat". *Dev Neurosci.* (2007) 29, 373-384.
Jurga et al., "Overview of General and Discriminating Markers of Differential Microglia Phenotypes," Front Cell Neurosci, 14: 198 (18 pages) (2020).

Kamiya., "Characteristics and problems of cascade impactors in the evaluation of inhaled preparations," Journal of Pharmaceutical Science and Technology, Japan, 65(4): English Machine Translation (5 pages)(2005).
Kay et al., "Disodium cromoglycate inhibits activation of human inflammatory cells in vitro," J Allergy Clin Immunol, 80(1): 1-8 (1987).
Keizman D. et al. Low-grade systemic inflammation in patients with amyotrophic lateral sclerosis. *Acta Neurol Scand.* (2009) 119:383-389.
Kondo et al., "iPSC-Based Compound Screening and In Vitro Trials Identify a Synergistic Anti-amyloid β Combination for Alzheimer's Disease," Cell Rep, 21: 2304-2312 (2017).
Lee, P.H. et al., "Circulating beta amyloid protein is elevated in patients with acute ischemic stroke". *J. Neural. Transm. (Vienna)*. (2005) 112, 1371-9.
Lehman, L.L. and Rivkin, M.J., "Perinatal arterial ischemic stroke: Presentation, risk factors, evaluation, and outcome". *Pediatr. Neurol.* (2014) 51, 760-768.
Lewis et al., "Quantification of Alzheimer pathology in aging and dementia: age-related accumulation of amyloid-β (42) peptide in vascular dementia," Neuropathology and Applied Neurobiology, 32(2): 103-118 (2006).
Li et al., "TREM2 regulates innate immunity in Alzheimer's disease," J Neuroinflammation, 15: 107 (7 pages) (2018).
Liu, Y.H. et al., "Aβ is predictive for short-term neurological deficits after acute ischemic stroke". *Neurotox Res.* (2015) 27, 292-299.
Lobo-Silva et al., "Balancing the immune response in the brain: IL-10 and its regulation," J Neuroinflammation, 13: 297 (10 pages) (2016).
Madureira, S. et al., "Dementia and cognitive impairment three months after stroke". *Eur J Neurol* (2001) 8, 621-627.
Mattson, M.P. et al., "Cellular signaling roles of TGFβ, TNF α and α APP in brain injury responses and Alzheimer's disease". *Brain Res. Brain Res. Rev.* (1997) 23, 47-61.
McArthur et al., "Annexin A1: a central player in the anti-inflammatory and neuroprotective role of microglia," J Immunol 185: 6317-6328 (2010).
McGeer et al. "Targeting microglia for the treatment of Alzheimer's disease," Expert Opin Ther Targets 19: 497-506 (2015).
Moreau C. et al. Elevated IL-6 and TNF-alpha levels in patients with ALS: inflammation or hypoxia. Neurology. (2005) 65:1958-1960.
Müller et al., "Fluorine in Pharmaceuticals: Looking Beyond Intuition," Science, 317: 1881 (2007).
Nagamoto-Combs et al., "Microglial phenotype is regulated by activity of the transcription factor, NFAT (nuclear factor of activated T cells)," J Neurosci, 30(28): 9641-9646 (2010).
Noristani et al., "RNA-Seq Analysis of Microglia Reveals Time-Dependent Activation of Specific Genetic Programs following Spinal Cord Injury," Front Mol Neurosci, 10: 90 (16 pages) (2017).
Onderdijk et al., "IL-4 Downregulates IL-1β and IL-6 and Induces GATA3 in Psoriatic Epidermal Cells: Route of Action of a Th2 Cytokine," J Immunol, 195:1744-1752 (2015).
Orr et al., "A Brief Overview of Tauopathy: Causes, Consequences, and Therapeutic Strategies," Trends in Pharmacological Sciences, 38(7): 637-648 (2017).
Panza et al., "Emerging drugs to reduce abnormal [beta]-amyloid protein in Alzheimer's disease patients," Expert Opin Emerging Drugs, 21(4): 377-391 (2016).
Parajuli et al., "CCL11 enhances excitotoxic neuronal death by producing reactive oxygen species in microglia," Glia, 63: 2274-2284 (2015).
Parameswaran et al., "Tumor necrosis factor-α signaling in macrophages," Crit Rev Eukaryot Gene Expr, 20(2): 87-103 (2010).
Park, J.H. et al., "Pathogenesis of cerebral microbleeds: In vivo imaging of amyloid and subcortical ischemic small vessel disease in 226 individuals with cognitive impairment". *Ann. Neurol.* (2013) 73, 584-593.
Philips T. and Robberecht W. "Neuroinflammation in amyotrophic lateral sclerosis: role of glial activation in motor neuron disease". *Lancet Neurol.* (2011) 10(3):253-263.

(56) References Cited

OTHER PUBLICATIONS

Radicava (edaravone) US Prescribing Information. Jersey City, New Jersey: MT Pharma America, Inc; May 2017.
Raivich, G. et al., "Neuroglial activation repertoire in the injured brain: graded response, molecular mechanisms and cues to physiological function". *Brain Res. Brain Res. Rev.* (1999) 30, 77-105.
Richards et al., "Neurodegenerative diseases have genetic hallmarks of autoinflammatory disease," Hum Mol Genet, 27(R2): R108-R118 (2018).
Rilutek (riluzole) Tablets: US prescribing information. Cary, NC, USA: Covis Pharmaceuticals, Inc; 1995. (Revised Apr. 2016).
Saleh I.A. et al. Evaluation of humoral immune response in adaptive immunity in ALS patients during disease progression. *J Neuroimmunol.* (2009) 215:96-101.
Sandoval, K.E., and Witt, K.A., "Blood-brain barrier tight junction permeability and ischemic stroke". *Neurobiology of Disease* (2008) 32, 200-219.
Sawada et al., "Induction of functional interleukin-2 receptor in mouse microglia," J Neurochem, 64: 1973-1979 (1995).
Schilling, M. et al., "Microglial activation precedes and predominates over macrophage infiltration in transient focal cerebral ischemia: a study in green fluorescent protein transgenic bone marrow chimeric mice".*Exp Neurol* (2003) 183, 25-33.
Shah et al., "The role of fluorine in medicinal chemistry," J Enzyme Inhib Med Chem, 22(5): 527-540 (2007).
Sheng et al., "Tumor necrosis factor alpha upregulates human microglial cell production of interleukin-10 in vitro," Clin Diagn Lab Immunol, 2(5): 604-608 (1995).
Shoup et al., "Fluorinated Cromolyn Derivatives for Potential Alzheimer's Disease Treatment," J Nucl Med 60, 114 (2019).
Silverstein, F.S. et al., "Cytokines and perinatal brain injury". *Neurochem Int* (1997) 30, 375-383.
Sinniah et al., "The Anti-allergic Cromones: Past, Present, and Future," Front Pharmacol, 8:827 (10 pages) (2017).
Sousa et al., "Cellular and Molecular Characterization of Microglia: A Unique Immune Cell Population," Front Immunol, 8(198): 1-18 (2017).
Subramaniam et al., "Targeting Microglial Activation States as a Therapeutic Avenue in Parkinson's Disease," Front Aging Neurosci, 9(176): 1-18 (2017).
Sun et al., "Fluorinated molecules as drugs and imaging agents in the CNS," Curr Top Med Chem, 6(14): 1457-1464 (2006).

Tanaka, R. et al., "Migration of enhanced green fluorescent protein expressing bone marrow-derived microglia/macrophage into the mouse brain following permanent focal ischemia," *Neuroscience* (2003) 117, 531-539.
Thériault et al., "The dynamics of monocytes and microglia in Alzheimer's disease," Alzheimer's Res Ther, 7:41 (10 pages) (2015).
Tiglutik (riluzole) oral suspension: US prescribing information. Berwyn, PA, USA: ITF Pharma, Inc; 1995 (Revised Sep. 2018).
Trias et al., "Phenotypic transition of microglia into astrocyte-like cells associated with disease onset in a model of inherited ALS," Front Cell Neurosci, 7: 274 (8 pages) (2013).
US FDA Guidance for Industry Suicidal Ideation and Behavior: Prospective Assessment of Occurrence in Clinical Trials (2012).
Wake et al., "Resting Microglia Directly Monitor the Functional State of Synapses In Vivo and Determine the Fate of Ischemic Terminals," J Neurosci, 29(13): 3974-3980 (2009).
Walker et al., "Immune phenotypes of microglia in human neurodegenerative disease: challenges to detecting microglial polarization in human brains," Alzheimer's Res Ther, 7:56 (9 pages) (2015).
Wen, Y. et al., "Increased beta-secretase activity and expression in rats following transient cerebral ischemia," *Brain Res*. (2004) 1009, 1 -8.
Wilcock et al., "Changing Perspective on the Role of Neuroinflammation in Alzheimer's Disease," Int J Alzheimers Dis, 2012: 495243 (7 pages) (2012).
Wilhelmsson et al., "Injury Leads to the Appearance of Cells with Characteristics of Both Microglia and Astrocytes in Mouse and Human Brain," Cereb Cortex, 27(6): 3360-3377 (2017).
Yang et al., "Increased levels of MIP-1α in CSF and serum of ALS," Acta Neurologica Scandinavica, 134(2): 94-100 (2016).
Zekry, D. et al., "The vascular lesions in vascular and mixed dementia: the weight of functional neuroanatomy," *Neurobiol Aging* (2003) 24, 213-219.
Zhang et al., "Cromolyn Reduces Levels of the Alzheimer's Disease-Associated Amyloid β-Protein by Promoting Microglial Phagocytosis," Sci Rep, 8:1144 (9 pages) (2018).
Zhao et al., "Microglia-targeting nanotherapeutics for neurodegenerative diseases," APL Bioeng, 4:030902 (17 pages) (2020).
Zhu et al., "Pharmacy," Fourth Military Medical University Press, 309, (2007).

\* cited by examiner

POWDERED FORMULATIONS OF CROMOLYN SODIUM AND ALPHA-LACTOSE

This application is a continuation of PCT International Patent Application No. PCT/US19/40247, filed Jul. 2, 2019, which claims the benefit of priority to U.S. Provisional Patent Application No. 62/692962, filed Jul. 2, 2018, the contents of both of which are incorporated herein by reference in their entirety.

BACKGROUND

Therapies to prevent Alzheimer's Disease (AD) progression remain a high-unmet medical need. US Food and Drug Administration (FDA) approved acetylcholinesterase (AChE) inhibitor drugs, such as donepezil, rivastigamine and galantamine are indicated for symptomatic relief in persons with mild to moderate AD (Cummings J L, "Alzheimer's disease," *N Engl J Med* (2004) 351, 56-67; Knowles J, "Donepezil in Alzheimer's disease: an evidence-based review of its impact on clinical and economic outcomes," *Core Evidence* (2006) 1, 195-219). These drugs increase levels of available acetylcholine during synaptic transmission and thus compensate for the diminished function of cholinergic neurons. However, none of the drugs approved for AD are disease-modifying treatments that affect the underlying pathophysiology of the disease, so the duration of their benefit is short-term (Knowles, 2006). The development of successful disease-modifying treatments, in contrast, would have a long-term beneficial outcome on the course of AD progression.

The treatment of AD will require addressing the multiple triggers of pathogenesis. There are two primary neuropathologies in the brains of AD patients: i) extracellular protein plaques principally composed of Aβ peptides, also known as amyloid plaques; and ii) intracellular tangles of fibrils composed of tau protein found inside of neurons, also known as tau tangles. The advent and spread of neurotoxic oligomeric aggregates of Aβ is widely regarded as the key trigger leading to neuronal damage, which then leads to the accumulation of intracellular tau tangles, and finally to neuronal cell death in AD pathogenesis.

Beta-amyloid peptides (37 to 43 amino acids in length) are formed by sequential cleavage of the native amyloid precursor protein (APP) (Karran et al., "The amyloid cascade hypothesis for Alzheimer's disease: an appraisal for the development of therapeutics," *Nature Reviews* (2011) 10, 698-712). Aberrant Aβ peptide isoforms that are 40 or 42 amino acids in length (Aβ40 and 42) misfold into aggregates of oligomers that grow into fibrils that accumulate in the brain as amyloid plaques. More importantly for AD pathogenesis, the alternate fate of Aβ oligomers is to become trapped in neuronal synapses where they hamper synaptic transmission, which eventually results in neuronal degeneration and death (Haass et al., "Soluble protein oligomers in neurodegeneration: lessons from the Alzheimer's amyloid β-peptide," *Nature Reviews Mol. Cell Biol.* (2007) 8:101-112; Hashimoto et al, "Apolipoprotein E, especially apolipoprotein E4, increases the oligomerization of amyloid beta Peptide," *J. Neurosci.* (2012) 32, 15181-15192).

The cascade of Aβ oligomer-mediated neuronal intoxication is exacerbated by another AD trigger: chronic local inflammatory responses in the brain (Krstic et al., "Deciphering the mechanism underlying late-onset Alzheimer disease," *Nature Reviews Neurology* (2013), January, 9 (1): 25-34). Alzheimer's disease has a chronic neuro-inflammatory component that is characterized by the presence of abundant microglial cells associated with amyloid plaque. (Heneka et al., "Acute treatment with the PPAR$_\gamma$ agonist pioglitazone and ibuprofen reduces glial inflammation and Abeta1-42 levels in APPV717I transgenic mice," *Brain* (2005) 128, 1442-1453; Imbimbo et al., "Are NSAIDs useful to treat Alzheimer's disease or mild cognitive impairment," *Front. Aging Neurosci* (2010) 2 (article 19), 1-14). These cyclooxygenase (COX1/COX2)-expressing microglia, which phagocytose amyloid oligomers, become activated to secrete pro-inflammatory cytokines. (Hoozemans et al., "Soothing the inflamed brain: effect of non-steroidal anti-inflammatory drugs on Alzheimer's disease pathology," *CNS & Neurological Disorders—Drug Targets* (2011) 10, 57-67; Griffin T S., "What causes Alzheimer's?" *The Scientist* (2011) 25, 36-40; Krstic 2013). This neuro-inflammatory response, besides promoting local vascular leakage through the blood brain barrier (BBB). Zlokovic (Zlokovic B., "Neurovascular pathways to neurodegeneration in Alzheimer's disease and other disorders," *Nature Reviews Neurosci.* (2011) 12, 723-738) has been implicated in driving further production of aberrant Aβ peptides 40 and 42 via modulation of gamma-secretase activity (Yan et al., "Anti-inflammatory drug therapy alters β-amyloid processing and deposition in an animal model of Alzheimer's disease," *J. Neurosci.* (2003) 23, 7504-7509; Karran 2011) and to be detrimental to hippocampal neurogenesis in the adult brain (Gaparini et al., "Non-steroidal anti-inflammatory drugs (NSAIDs) in Alzheimer's disease: old and new mechanisms of action," *J. Neurochem* (2004) 91, 521-536). Thus, neuro-inflammation, in combination with amyloid oligomer-mediated neuronal intoxication, creates a cycle that results in progressive neural dysfunction and neuronal cell death spreading throughout the brain in subjects with AD.

Compelling evidence from multiple epidemiology studies revealed that long-term dosing with non-steroidal anti-inflammatory drugs (NSAIDs) dramatically reduced AD risk in the elderly, including delayed disease onset, reduced symptomatic severity and slowed cognitive decline. (Veld et al., "Nonsteroidal anti-inflammatory drugs and the risk of Alzheimer's disease," *N. Engl. J. Med* (2001) 345, 1515-1521; Etminan et al., "Effect of non-steroidal anti-inflammatory drugs on risk of Alzheimer's disease: systematic review and meta-analysis of observational studies," *Brit. Med. Journal* (2003) 327, 1-5; Imbimbo, 2010). Three mechanisms have been proposed for how NSAIDs inhibit the processes that contribute to AD progression: i) by inhibiting COX activity to reduce or prevent microglial activation and cytokine production in the brain (Mackenzie, et al., "Nonsteroidal anti-inflammatory drug use and Alzheimer-type pathology in aging," *Neurology* (1998) 50, 986-990; Alafuzoff et al., "Lower counts of astroglia and activated microglia in patients with Alzheimer's disease with regular use of non-steroidal anti-inflammatory drugs," *J. Alz. Dis.* (2000) 2, 37-46; Yan, 2003; Gasparini, 2004; Imbimbo, 2010); ii) by reducing amyloid deposition (Weggen et al., "A subset of NSAIDs lower amyloidogenic Abeta42 independently of cyclooxygenase activity," *Nature* (2001) 414, 212-216; Yan, 2003; Imbimbo, 2010); or iii) by blocking COX-mediated prostaglandin E2 responses in synapses (Kotilinek et al., "Cyclooxygenase-2 inhibition improves amyloid-β-mediated suppression of memory and synaptic plasticity," *Brain* (2008) 131, 651-664.

Therefore, NSAIDs are predicted to dampen the neuroinflammatory response and impact AD progression via several mechanisms. When administered together with drugs that inhibit Aβ oligomerization, the combination treatment paradigm is proposed to attenuate the multiple triggers leading to neurodegeneration and neuronal death. The decline in cognitive performance may be reversed, due to neuronal plasticity and neurogenesis in the hippocampus (Kohman et al., "Neurogenesis, inflammation and behavior," *Brain, Behavior, and Immunity* (2013) 27, 22-32), if AD progression is arrested at a very early stage.

BRIEF SUMMARY

The present disclosure relates to a composition comprising, consisting essentially of, or consisting of cromolyn sodium, α-lactose, and salt of a fatty acid, wherein the cromolyn sodium, α-lactose, and salt of a fatty acid are micronized, and wherein the α-lactose has a particle size distribution of $D_{90}$ of 45-70 μm, $D_{50}$ of 10-35 μm, and $D_{10}$ of 2-13 μm.

The present disclosure relates to a method of treating a disorder selected from Alzheimer's disease, amyloidosis-associated condition (AAC), traumatic brain injury, Huntington's disease, atherosclerosis, cytokine release syndrome (CRS), dementia, head injury, infection, neuroinflammation, prion disease, stroke, amyotrophic lateral sclerosis (ALS), Parkinson's disease, and asthma in a subject in need thereof comprising administering a composition comprising, consisting essentially of, or consisting of cromolyn sodium, α-lactose, and salt of a fatty acid, wherein the cromolyn sodium, α-lactose, and salt of a fatty acid are micronized, and wherein the α-lactose has a particle size distribution of $D_{90}$ of 45-70 μm, $D_{50}$ of 10-35 μm, and $D_{10}$ of 2-13 μm.

DETAILED DESCRIPTION

The present disclosure relates to compositions for inhalation delivery. The present disclosure combines powdered forms of at least two excipients and an active ingredient for administration via inhalation. The composition can be used in formulations to enable enhanced delivery of the active ingredient into the deep lung regions, thereby increasing the bioavailability of the active ingredient in the plasma as well as uptake through the blood-brain barrier for treatment of neurological diseases. The presently disclosed compositions are capable of reaching the levels of bioavailability of the active ingredient in the plasma sufficient for neurological treatment, while other existing formulations of the active ingredient are designed to only treat the respiratory tract.

The present disclosure also relates to compositions for a dosage form via inhalation comprising the following components: cromolyn sodium, α-lactose, and a magnesium salt. Preferably, the magnesium salt is magnesium stearate. Not to be limited by theory, but it is believed that during blending, the α-lactose is shaped into a rounded form by shearing forces of the mixing, as well as by the adherence of the magnesium salt to the flat regions and crevices of the α-lactose particles. It is believed that there is greater adherence between α-lactose and the magnesium salt thereby coating the α-lactose, which in turn reduces the adhesive/cohesive forces between the carrier and the active ingredient, and between the particles of the active ingredient, allowing for easy release of the cromolyn during inhalation. This greater adherence, rounded particle shape, and smaller size of the α-lactose particles contribute to depositing the cromolyn deeper into the lung region thereby providing an effective dose with less cromolyn in the drug product form.

In particular, the present disclosure is applicable for patients with diseases that impair mental performance, such as Alzheimer's disease, thereby ensuring effective dose delivery with minimal effort of inhalation. Because of its versatility, the composition and formulation may also be used to treat other diseases including, but not limited to, stroke, amyotrophic lateral sclerosis (ALS), Parkinson's disease, and asthma.

One application of the present disclosure is a composition of cromolyn sodium and α-lactose each in powdered form suitable for inhalation as a combination dosage form. In this case, each ingredient is in powdered form to facilitate administration via inhalation and to enable easy and accurate dosing. The present disclosure is based in part upon the discovery that when cromolyn sodium and α-lactose are both in powdered form, α-lactose improves the aerodynamic flow of micronized cromolyn. This improvement allows for a higher concentration of cromolyn to reach deeper within the patient's lungs, thereby achieving the same therapeutic effect with less drug. Another advantage is that a perfect dosage via inhalation may not be necessary to achieve adequate therapeutic effect. Yet, another advantage is that the presence of α-lactose helps mask the bitter taste of cromolyn, thereby making administration pleasant. In patients with impaired physical abilities (which may be due to a disease such as Alzheimer's disease), a perfect inhalation (a perfect "puff") may not always be possible; with the present disclosure, even impaired inhalation (an imperfect "puff") will deliver sufficient drug dosage to treat the desired disease. The advantages of the present composition can be applied to other diseases with similar problems and expand the list of indications where the improved dosage form may be applicable.

In one application, the co-administration of the composition of cromolyn sodium, α-lactose, and a metallic salt of a fatty acid can be used for the treatment of certain neurological diseases. The neurological diseases include, but are not limited to, AD, ALS, Parkinson's disease, and the effects from stroke.

The α-lactose used in the composition for the formulation is in form that is suitable for inhalation. In particular, the α-lactose particles are smoothed and rounded to allow for better carrier properties. The α-lactose particles are larger than the particle they carry, thus a larger particle distribution is mostly of larger particles. The smoother surfaces and edges prevent the API from being trapped in the carrier particle. Another prerequisite is that the α-lactose combines well with cromolyn sodium in order to enhance the delivery of cromolyn sodium via inhalation. In particular, the combination should deliver cromolyn sodium to the deep parts of the lung, e.g., DPI 4moc (stage 4 to MOC, representing the area of the lung consisting of the secondary bronchi to the alveoli).

α-Lactose was characterized to determine the parameters necessary to administer a therapeutically effective amount using an inhalation delivery system. The methodology included particle size determination (PSD); powdered x-ray crystallization diffraction (PXRD); and gravimetric vapor sorption (GVS).

The present disclosure relates to formulations wherein the α-lactose has a particle size distribution of $D_{90}$ of 45-70 μm, $D_{50}$ of 10-35 μm, and $D_{10}$ of 3-13 μm, preferably $D_{90}$ of 50-65 μm, $D_{50}$ of 15-30 μm, and $D_{10}$ of 5-10 μm, and more preferably $D_{90}$ of 50-60 μm, $D_{50}$ of 20-25 μm, and $D_{10}$ of 3-6 μm.

Cromolyn used in the composition formulation may primarily be manufactured for inhalation. Generally, the cromolyn is micronized. The present disclosure relates to a composition having cromolyn, where the cromolyn has a size parameter of about <10 μm; however, particle size may also include <5 μm. The cromolyn micronization produces an ultra-fine powder (d<10 μm) of small particle size. Micronized cromolyn typically has a specification of $D_{90} \leq 5$ μm.

The formulation also comprises a lubricant/stabilizer, which may be any pharmaceutically acceptable metallic salts of fatty acids such as stearic acid and its metallic salts. Acceptable stearic acids include, but are not limited to, magnesium stearate, calcium stearate, zinc stearate. A preferred stearic acid is magnesium stearate. The magnesium salt is micronized in a manner to create sufficiently small particles to work as a lubricant in conjunction with the carrier, lactose monohydrate to minimize agglomeration and improve carrier performance by reducing adhesion/cohesive forces between the carrier and cromolyn. Another advantage of using micronized magnesium salt is improved mixing and flow of the blend during encapsulation.

The present disclosure also relates to a composition of cromolyn sodium, α-lactose and magnesium stearate for delivery via inhalation. This composition comprises micronized cromolyn sodium, micronized α-lactose and magnesium stearate, wherein the α-lactose is prepared for inhalation and preferably has a particle size as mentioned above.

The composition improves the delivery of cromolyn, for example as compared to cromolyn only compositions or where cromolyn is delivered in sequence (not simultaneously) with α-lactose. For instance, the inhaled formulation of cromolyn only can deliver a therapeutically effective amount of cromolyn to the deep lung of about 23% to about 29% of the dosed amount. In contrast, it was found that the composition of the present disclosure delivered a therapeutically effective amount of cromolyn in a range of about 34% to about 53% and preferably 35% to about 44% of the dosed amount.

The compositions of the disclosure comprise about 45-65% by weight of cromolyn sodium, about 30-50% by weight of α-lactose, and about 1-5% by weight of magnesium stearate. A preferred composition comprises about 50-60% by weight of cromolyn sodium, about 35-45% by weight of α-lactose, and about 1-3% by weight of magnesium stearate. More preferably, the composition comprises about 58% by weight of cromolyn sodium, about 40% by weight of α-lactose, and about 2% by weight of magnesium stearate. As used herein, unless otherwise indicated, the term "cromolyn" includes cromolyn, cromolyn sodium, and other forms of pharmaceutically acceptable salts of cromolyn.

Formulation 1

| Component | Function | % w/w | mg/capsule |
|---|---|---|---|
| Cromolyn sodium (micronized) | Active Ingredient | 58 | 17.1 (±1.7) |
| Lactose Monohydrate | Diluent | 40 | 12.8 (±0.64) |
| Magnesium stearate (micronized) | Stabilizer | 2 | 0.6 (±0.03) |
| | | 100 | 32.0 (±2.4) |

Typically, the weight ratio of cromolyn sodium to α-lactose is about 1.7:1.12 to about 1.7:1.28, preferably, from about 1.7:1.34 to about 1.7:28, and more preferably from about 1.7:1.28.

The formulation includes a salt of fatty acid as a pharmaceutical lubricant, such as magnesium stearate. Typically, the weight ratio of cromolyn sodium to magnesium stearate is about 1.7:0.057 to about 1.7:0.06, preferably, from about 1.7:0.064 to about 1.7:0.6, and more preferably from about 1.7:0.06.

The formulations using micronized cromolyn, α-lactose, and a salt of fatty acid as a pharmaceutical lubricant provided improved performance of an inhaled substance when compared to the cromolyn only formulation. The formulated product batches had a comparable emitted dose as the six clinical batches produced of the cromolyn only product. The delivery of cromolyn alone resulted in the mean of 1.98% of the product reaching the deep lung area based on the NGI test results summation of Stage 4-MOC, whereas with combination of cromolyn, α-lactose, and magnesium stearate had a mean result of 39.5% of the inhaled cromolyn reaching the deep lung area. Therefore, the compositions of the present disclosure include cromolyn, α-lactose, and magnesium stearate composition having a mean result of 34% to 44.3% of the inhaled cromolyn reaching the deep lung area. As used herein, unless otherwise defined, the term "lung area" refers to Stage 4—MOC.

As illustrated in the data of Table 1, formulations of the present disclosure have a cromolyn percent emitted dose from 34% to 44% in the deep lung regions in comparison to a cromolyn only formulation having only 1.98% of emitted dose. Further, the compositions of the present disclosure deposited from 5.3 to 6.5 mg of cromolyn in stage 4-MOC.

TABLE 1

Performance of the cromolyn, α-lactose, and magnesium stearate formulation in inhalation tests.

| Batch # | Cromolyn Lot # | Lactose Lot # | Magnesium Stearate Lot # | Emitted dose Mean Range (mg) (% of dose) | Amount of drug in deep lung (stage 4-MOC)(mg) | % of emitted dose (stage 4 to MOC) |
|---|---|---|---|---|---|---|
| 1 | 13-0105 | 13-0094 | 14-0035 | 15.5 (90.6%) | 5.92 | 38.19 |
| 2 | 15-0013 | 13-0094 | 14-0035 | 15.63 (91.4%) | 5.32 | 34.03 |
| 3 | 15-0079 | 15-0066 | 15-0077 | 14.8 (86.5%) | 6.2 | 42.03 |
| 4 | 15-0079 | 15-0066 | 15-0077 | 16.61 (97.1%) | 6.3 | 37.93 |
| 5 | 15-0079 | 15-0066 | 15-0077 | 15.46 (90.4%) | 6.16 | 39.84 |
| 6 | 15-0079 | 15-0066 | 15-0077 | 14.86 (86.9%) | 6.2 | 41.72 |
| 7 | 15-0014 | 15-0066 | 15-0077 | 14.67 (85.8%) | 6.5 | 44.31 |
| 8 | 15-0079 | 15-0066 | 18-0038 | 14.97 (87.5%) | 5.7 | 38.07 |
| 9 | n/a | absent | absent | 16.6 (97%) | 0.33 | 1.98 |

Particle size distribution of the components of the tested formulation are shown in Tables 2, 3, and 4:

TABLE 2

Cromolyn API (micronized)

| Lot # | $D_{10}$ (µm) | $D_{50}$ (µm) | $D_{90}$ (µm) |
|---|---|---|---|
| 13-0105 | 0.5 | 1.9 | 4.6 |
| 15-0013 | 0.6 | 1.8 | 3.8 |
| 15-0079 | — | — | 4.2 |

TABLE 3

α-Lactose (DFE Pharma Lactohale LH201)

| Lot# | $D_{10}$ (3-6 µm) | $D_{50}$ (20-25 µm) | $D_{90}$ (50-60 µm) |
|---|---|---|---|
| 13-0094 | 3 | 21 | 54 |
| 15-0066 | 4 | 23 | 57 |
| 16-0127 | 3 | 22 | 59 |

TABLE 4

Magnesium Stearate (micronized)

| Lot | $D_{50}$ (<5 µm) | $D_{90}$ (<10 µm) |
|---|---|---|
| 14-0035 | 3.56 | 6.74 |
| 15-0077 | 4.82 | 9.28 |
| 18-0038 | 4.33 | 8.04 |

During respiration of particles, particles <3 µm in size will deposit in the lower regions of the lung which are then adsorbed. Table 1 demonstrates formulation performance and demonstrates that a larger amount of API reached the lower lung, compared to cromolyn alone. Based on the particle distribution of the cromolyn ($D_{90} \leq 5$ µm), most batches had a particle distribution for $D_{90}$ that ranged from ≤5 µm to ≥3.5 µm. If such particles were inhaled without the α-lactose and magnesium stearate of the disclosure, cromolyn would deposit mostly in the oropharynx and upper respiratory tract, and would thus be less effective. It is believed that the ultrafine particles <3 µm size may be exhaled before contact with lung tissue. Also, these particles make up only a fraction of the dose. It is imperative to have the particles in the range of 5 µm to 3 µm in the lower regions of the lung for adsorption as they make up 90% of the API in the mixture.

Comparison experiments using inhalers Spinhaler® and Cyclohaler® delivering composition consisting of cromolyn and lactose (Tables 5-7) demonstrate significantly lower ranges of the emitted dose (60% to 78%), compared to the data presented in Table 1 (Gilani et al, "Influence of formulation variables and inhalation device on the deposition profiles of cromolyn sodium dry powder aerosols," *DARU J. Pharm. Sci.* (2004) 12(3), 123-130).

TABLE 5

Particle size distribution of α-Lactose and cromolyn sodium.

| Particles | $D_{10}$ | $D_{50}$ | $D_{90}$ |
|---|---|---|---|
| P450M* | 2.5 ± 0.3 | 12.3 ± 0.8 | 26.5 ± 0.3 |
| P325M* | 6.6 ± 0.8 | 53.5 ± 4.3 | 74.1 ± 3.8 |
| Cromolyn Sodium | 0.7 ± 0.1 | 1.52 ± 0.2 | 3.03 ± 0.02 |

*P450 - Pharmatose P450 α-Lactose; P325 - Pharmatose P325 α-Lactose.

TABLE 6

Performance of the cromolyn and α-lactose formulation in inhalation tests using Spinhaler ®.

| Formulation | Recovered Dose mg (% Recovered) | Fine Particle Dose (mg) | Emitted Dose mg (% Dose) |
|---|---|---|---|
| CS-P450 (70:30) | 18.95 (94.75%) | 2.87 | 13.74 (68.7%) |
| CS-P450 (50:50) | 19.02 (95.1%) | 3.71 | 14.19 (70.95%) |
| CS-P325 (70:30) | 18.98 (94.9%) | 1.76 | 12.57 (62.85%) |
| CS-P325 (50:50) | 19.12 (95.6%) | 3.05 | 12.80 (64%) |

CS—Cromolyn sodium (20 mg)

TABLE 7

Performance of the cromolyn and α-lactose formulation in inhalation tests using Cyclohaler ®.

| Formulation | Recovered Dose mg (%) | Fine Particle Dose (mg) | Emitted Dose mg (% Dose) |
|---|---|---|---|
| CS-P450 (70:30) | 19.16 (95.8%) | 5.92 | 15.34 (76.7%) |
| CS-P450 (50:50) | 19.15 (95.75%) | 7.12 | 15.64 (78.2%) |
| CS-P325 (70:30) | 18.96 (94.8%) | 4.40 | 11.97 (59.85%) |
| CS-P325 (50:50) | 19.09 (95.45%) | 6.05 | 13.12 (65.6%) |

CS—Cromolyn sodium (20 mg)

The formulations of the disclosure may include additional pharmaceutically acceptable excipients. Pharmaceutically acceptable excipients for dry powdered inhalers include, but are not limited to, lactose monohydrate and magnesium stearate.

The present disclosure relates to methods of making the described compositions comprising α-lactose (inhalation grade); micronizing cromolyn; and micronizing magnesium stearate. It is understood that we shall refer to magnesium stearate however other pharmaceutical lubricants suitable for inhalation are equally applicable. The method of making the formulation of the present disclosure relates to α-lactose; micronizing cromolyn; and micronizing magnesium stearate. The blending may use a layering principle to ensure the even distribution of components. In some embodiments, cromolyn is dispensed in three equal parts. A method of making the formulation comprises placing a first part of cromolyn with a layer of magnesium stearate, adding a second part of cromolyn with a layer of lactose, and adding a third part of cromolyn to the layered mixture. Thereafter, the layered mixture is mixed. An alternative method of making the formulation of the present disclosure relates to first mixing lactose with magnesium stearate, dividing the blended lactose/magnesium stearate blend into three equal parts, separately mixing each part of the blend with a third part of cromolyn, layering each part of the cromolyn, lactose/magnesium stearate blend, and repeating the layering step two more times, mixing the layered mixture for 5 to 10 minutes but not more than 15 min with a high sheer blender at 500±2 rpm to yield a blend uniformity of 90-110% label claim.

Each component can be micronized using standard equipment commonly used in the pharmaceutical arts.

The present disclosure relates to a composition comprising cromolyn sodium, α-lactose, and salt of a fatty acid, wherein the cromolyn sodium, α-lactose, and salt of a fatty acid are micronized, and wherein the α-lactose has a particle size distribution of $D_{90}$ of 45-70 µm, $D_{50}$ of 10-35 µm, and $D_{10}$ of 2-13 µm.

In some embodiments, the salt of a fatty acid is selected from magnesium stearate, calcium stearate, and zinc stearate, for example, magnesium stearate.

In certain embodiments, the α-lactose is in a form of particles.

In some embodiments α-lactose particles are spheres or spheroids.

In certain embodiments, α-lactose has a particle size distribution of $D_{90}$ of 50-65 µm, $D_{50}$ of 15-30 µm, and $D_{10}$ of 5-10 µm, for example, particle size distribution of $D_{90}$ of 50-60 µm, $D_{50}$ of 20-25 µm, and $D_{10}$ of 3-6 µm.

In some embodiments, cromolyn sodium has a particle size distribution of $D_{90} \leq 5$ µm, for example, particle size distribution range of $D_{90} \leq 5$ µm to $\geq 3.5$ µm.

In certain embodiments, the composition comprises about 45-65% by weight of cromolyn sodium, about 30-50% by weight of α-lactose, and about 1-5% by weight of magnesium stearate, for example, the composition comprises about 50-60% by weight of cromolyn sodium, about 35-45% by weight of α-lactose, and about 1-3% by weight of magnesium stearate, such as about 58% by weight of cromolyn sodium, about 40% by weight of α-lactose, and about 2% by weight of magnesium stearate.

In some embodiments, the composition comprises about 17.1 mg of cromolyn sodium.

The present disclosure relates to a method of treating a disorder selected from Alzheimer's disease, amyloidosis-associated condition (AAC), traumatic brain injury, Huntington's disease, atherosclerosis, cytokine release syndrome (CRS), dementia, head injury, infection, neuroinflammation, prion disease, stroke, amyotrophic lateral sclerosis (ALS), Parkinson's disease, and asthma in a subject in need thereof. For example, the disorder is Alzheimer's disease. Alternatively, the disorder is amyloidosis-associated condition (AAC). Alternatively yet, the disorder is traumatic brain injury.

In certain embodiments, the disorder is Huntington's disease. Alternatively, the disorder is atherosclerosis. Alternatively yet, the disorder is CRS.

In some embodiments, the disorder is dementia. Alternatively, the disorder is head injury. Alternatively yet, the disorder is infection.

In certain embodiments, the disorder is neuroinflammation. Alternatively, the disorder is prion disease. Alternatively yet, the disorder is stroke.

In some embodiments, the disorder is ALS. Alternatively, the disorder is Parkinson's disease. Alternatively yet, the disorder is asthma.

In some embodiments, the composition is administered by oral inhalation.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXAMPLES

Example 1: Batch Formulation

Cromolyn sodium (1,160 g) was divided into three parts. Part 1 (381.5 g); Part 2 399.8 g) and Part 3 (379.5 g). Part 1 was placed into a shear batch mixer 10 L TRV mixing bowl. Magnesium stearate (40 g) was sprinkled onto Part 1 cromolyn sodium in the bowl. Part 2 cromolyn sodium was added to the bowl, followed by layering of lactose monohydrate (800 g). Part 3 cromolyn sodium was added to the top of the lactose monohydrate layer and the bowl was closed. The mixture was mixed for 15 minutes at 500 rpm to obtain a 2 kg batch formulation.

Example 2: Particle Size Distribution and Emitted Dose Measurements

Formulation Preparation

The blend of cromolyn sodium (58% by weight), α-lactose (58% by weight), and magnesium stearate (2% by weight) was encapsulated in size 3 HPMC capsules, each containing 32 mg of a blend containing a 17.1 mg cromolyn sodium.

Emitted Dose Measurements

For the emitted dose analysis, a single capsule containing the cromolyn sodium, α-lactose, and magnesium stearate formulation was placed in the inhaler device and pierced. The Plastiape RS01 dry powder inhaler (DPI) was loaded into the mouthpiece adapter and then into the induction port of the Copley TPK Flow Controller. The flow controller was set for a flow rate of 80±0.5 L/s for a 3 second pulse. Once the device was loaded into the flow controller, the flow controller was activated delivering the dose. The emitted powder was collected into a sample tube for HPLC analysis, determining the amount of product released from the capsule and device. The results of the measurements are shown in Table 2.

Particle Size Distribution Measurements

Aerodynamic particle size distribution analysis was performed using a Next Generation Impactor (NGI). A capsule containing the cromolyn sodium, α-lactose, and magnesium stearate formulation was loaded into the Plastiape RS01 DPI and pierced prior to loading onto the Copley flow controller. The controller was set for a flow rate of 80±0.5 L/s for a 3 second pulse. The NGI was setup for the test where a coating solution of 3% v/v glycerol, 0.1% w/v Lutrol F-68 in acetone was placed in each NGI stage cup (1 through 7 plus a Micro-orifice collector (MOC)). The loaded inhaler device was inserted into the mouthpiece adapter, and the assembly was inserted into the induction port of the flow controller. The flow controller was activated for 3 seconds and upon completion samples were collected from the device, throat and mouth piece adapter, pre-separator on the NGI, and each stage cup on the NGI. A diluent was used to rinse the surface of each device into a sample tube for HPLC analysis. Following analysis of each sample, the amount of product capture was determined. The FPM (Fine Particle Mass) is the sum in (mg) of the NGI cups representing stage 3 through MOC. The results of the measurements are shown in Table 8.

TABLE 8

Particle Size Distribution and Emitted Dose Measurements

| Batch 1 | Result | Cromolyn | Particle size (μm) | α-Lactose | Particle size (μm) | Mg St* | Particle size (μm) |
|---|---|---|---|---|---|---|---|
| FPM | 5.3 mg | $D_{10}$ | 0.6 | $D_{10}$ | 3 | $D_{10}$ | 3.3 |
| Emitted Dose | 15.63 mg | $D_{50}$ | 1.8 | $D_{50}$ | 21 | $D_{50}$ | 8.3 |
| | | $D_{90}$ | 3.8 | $D_{90}$ | 54 | $D_{90}$ | 22.6 |

| Batch 2 | Result | Cromolyn | Particle size (μm) | α-Lactose | Particle size (μm) | $D_{10}$ | Particle size (μm) |
|---|---|---|---|---|---|---|---|
| FPM | 6.2 mg | $D_{10}$ | — | $D_{10}$ | 4 | $D_{10}$ | — |
| Emitted Dose | 14.8 mg | $D_{50}$ | — | $D_{50}$ | 23 | $D_{50}$ | 4.82 |
| | | $D_{90}$ | 4.2 | $D_{90}$ | 57 | $D_{90}$ | 9.28 |

| Batch 3 | Result | Cromolyn | Particle size (μm) | α-Lactose | Particle size (μm) | Mg St | Particle size (μm) |
|---|---|---|---|---|---|---|---|
| FPM | 5.7 mg | $D_{10}$ | 0.6 | $D_{10}$ | 3 | $D_{10}$ | — |
| Emitted Dose | 15.03 mg | $D_{50}$ | 1.8 | $D_{50}$ | 22 | $D_{50}$ | 4.33 |
| | | $D_{90}$ | 3.8 | $D_{90}$ | 59 | $D_{90}$ | 8.04 |

*Mg St—Magnesium Stearate

What is claimed is:

1. A composition comprising cromolyn sodium, α-lactose, and a salt of a fatty acid, wherein:
   the cromolyn sodium, α-lactose, and the salt of the fatty acid are micronized;
   the α-lactose has a particle size distribution of $D_{90}$ of 45-70 μm, $D_{50}$ of 10-35 μm, and $D_{10}$ of 2-13 μm;
   the composition comprises about 45-65% by weight of cromolyn sodium, about 30-50% by weight of α-lactose, and about 1-5% by weight of the salt of a fatty acid; and
   the composition is capable of being delivered using a device that deposits at least 30 wt. % of the administered amount of cromolyn sodium to Stage 4 and higher of a Next Generation Pharmaceutical Impactor (NGI) cascade impactor device at a flow rate of about 80 L/min.

2. The composition of claim 1, wherein the salt of the fatty acid is selected from magnesium stearate, calcium stearate, and zinc stearate.

3. The composition of claim 1, wherein the salt of the fatty acid is magnesium stearate.

4. The composition of claim 1, wherein the α-lactose particles are spheres or spheroids.

5. The composition of claim 1, wherein the α-lactose has a particle size distribution of $D_{90}$ of 50-65 μm, $D_{50}$ of 15-30 μm, and $D_{10}$ of 5-10 μm.

6. The composition of claim 1, wherein the α-lactose has a particle size distribution of $D_{90}$ of 50-60 μm, $D_{50}$ of 20-25 μm, and $D_{10}$ of 3-6 μm.

7. The composition of claim 1, wherein the cromolyn sodium has a particle size distribution of $D_{90} \leq 5$ μm.

8. The composition of claim 1, wherein the cromolyn sodium has a particle size distribution range from $D_{90}=5$ μm to $D_{90}=3.5$ μm.

9. The composition of claim 1, wherein the composition comprises about 58% by weight of cromolyn sodium, about 40% by weight of α-lactose, and about 2% by weight of magnesium stearate.

10. The composition of claim 1, wherein the composition comprises about 17.1 mg of cromolyn sodium.

11. A method of treating a disorder selected from Alzheimer's disease, amyloidosis-associated condition (AAC), traumatic brain injury, Huntington's disease, atherosclerosis, cytokine release syndrome (CRS), dementia, head injury, infection, neuroinflammation, prion disease, stroke, amyotrophic lateral sclerosis (ALS), Parkinson's disease, and asthma, comprising administering the composition of claim 1 to a subject in need thereof.

12. The method of claim 11, wherein the disorder is Alzheimer's disease.

13. The method of claim 11, wherein the disorder is stroke.

14. The method of claim 11, wherein the disorder is ALS.

15. The method of claim 11, wherein the disorder is Parkinson's disease.

16. The method of claim 11, wherein the disorder is asthma.

17. The method of claim 11, wherein the disorder is AAC.

18. The method of claim 11, wherein the disorder is traumatic brain injury.

19. The method of claim 11, wherein the disorder is Huntington's disease.

20. The method of claim 11, wherein the disorder is atherosclerosis.

21. The method of claim 11, wherein the disorder is CRS.

22. The method of claim 11, wherein the disorder is dementia.

23. The method of claim 11, wherein the disorder is head injury.

24. The method of claim 11, wherein the disorder is infection.

25. The method of claim 11, wherein the disorder is neuroinflammation.

26. The method of claim 11, wherein the disorder is prion disease.

27. The method of claim 11, wherein the composition is administered by oral inhalation.

* * * * *